United States Patent
Buchanan et al.

(10) Patent No.: US 8,696,903 B2
(45) Date of Patent: Apr. 15, 2014

(54) HIGH-PRESSURE TUBING

(75) Inventors: John Buchanan, Attleboro, MA (US); Dennis DellaRovere, Mendon, MA (US)

(73) Assignee: Waters Technologies Corporation, Milford, MA (US)

( * ) Notice: Subject to any disclaimer, the term of this patent is extended or adjusted under 35 U.S.C. 154(b) by 936 days.

(21) Appl. No.: 12/067,216

(22) PCT Filed: Sep. 14, 2006

(86) PCT No.: PCT/US2006/035892
§ 371 (c)(1),
(2), (4) Date: May 26, 2010

(87) PCT Pub. No.: WO2007/038003
PCT Pub. Date: Apr. 5, 2007

(65) Prior Publication Data
US 2010/0230954 A1 Sep. 16, 2010

Related U.S. Application Data

(60) Provisional application No. 60/719,070, filed on Sep. 21, 2005.

(51) Int. Cl.
*B01D 15/08* (2006.01)

(52) U.S. Cl.
USPC ........ 210/198.2; 210/656; 138/141; 138/143; 264/267; 285/381.1

(58) Field of Classification Search
USPC ........ 210/656, 198.2; 138/141, 143; 264/267; 285/381.1
See application file for complete search history.

(56) References Cited

U.S. PATENT DOCUMENTS

| | | | |
|---|---|---|---|
| 3,920,268 A | | 11/1975 | Stewing |
| 4,104,095 A | * | 8/1978 | Shaw ............................ 156/83 |
| 4,168,192 A | * | 9/1979 | Nyberg ........................ 156/86 |
| 4,377,894 A | * | 3/1983 | Yoshida ...................... 29/421.1 |
| 4,424,127 A | * | 1/1984 | Roeraade .................. 210/198.2 |
| 4,636,316 A | | 1/1987 | Harris et al. |

(Continued)

FOREIGN PATENT DOCUMENTS

| | | |
|---|---|---|
| EP | 0134566 | 3/1985 |
| JP | 59192552 | 10/1984 |

(Continued)

OTHER PUBLICATIONS

PTO Translation No. 12-5323 of Fukushima (Japan Patent No. H08-156098) Aug. 2012.*

(Continued)

*Primary Examiner* — Ernest G Therkorn
(74) *Attorney, Agent, or Firm* — Waters Technologies Corporation

(57) ABSTRACT

A method for making conduits includes inserting an inner tube into an outer tube and melting a portion of the inner tube to form a bond with the outer tube. The inner tube includes a polymeric material and the outer tube includes a material having a greater yield strength than the polymeric material. A conduit includes one or more inner tubes at least one of which is melt-bonded to one or more outer tubes. An analytical instrument includes a separation column, a solvent reservoir and pump, a sample injector, a detector to observe an eluent of the separation column, and tubing to transport fluid between components of the instrument.

13 Claims, 5 Drawing Sheets

(56) References Cited

U.S. PATENT DOCUMENTS

| | | | |
|---|---|---|---|
| 4,822,952 A * | 4/1989 | Katz et al. | 174/73.1 |
| 4,828,557 A * | 5/1989 | Persidsky | 604/408 |
| 4,842,305 A | 6/1989 | Kistenichi et al. | |
| 4,923,226 A | 5/1990 | Bartholomew | |
| 5,194,915 A | 3/1993 | Gilby | |
| 5,650,846 A | 7/1997 | Yin et al. | |
| 6,135,159 A * | 10/2000 | Karl | 138/139 |
| 6,199,921 B1 | 3/2001 | Cassel et al. | |
| 6,438,299 B1 * | 8/2002 | Brown et al. | 385/100 |
| 6,783,672 B2 * | 8/2004 | Tubbs et al. | 210/198.2 |
| 6,783,673 B2 * | 8/2004 | Horsman et al. | 210/198.2 |
| 2004/0035774 A1 | 2/2004 | Horsman et al. | |
| 2004/0080744 A1 | 4/2004 | Hobbs | |
| 2005/0052024 A1 * | 3/2005 | Herrington | 285/374 |
| 2006/0032816 A1 * | 2/2006 | Marcus et al. | 210/634 |
| 2006/0118194 A1 * | 6/2006 | Mechler et al. | 138/125 |
| 2006/0243651 A1 * | 11/2006 | Ricker | 210/198.2 |
| 2007/0068872 A1 * | 3/2007 | Gerhardt et al. | 210/656 |
| 2010/0000927 A1 * | 1/2010 | Beigel et al. | 210/198.2 |

FOREIGN PATENT DOCUMENTS

| | | |
|---|---|---|
| JP | 08156098 | 6/1996 |
| JP | 2003500646 | 1/2003 |
| JP | 2007512503 | 5/2007 |
| WO | 0204087 | 1/2002 |
| WO | 2005015162 | 2/2005 |
| WO | 2006130408 | 12/2006 |

OTHER PUBLICATIONS

Translation of Notice of Rejection for Japanese Patent Application No. 2008-532285, dated Dec. 14, 2011, 4 pages.

PCT International Search Report for Application No. PCT/US06/35892, Form PCT/ISA/220+210, date of completion Dec. 22, 2006, 3 pages.

PCT International Written Opinion for Application No. PCT/US06/35892, Form PCT/ISA/237, date of completion Dec. 22, 2006, 4 pages.

* cited by examiner

HIGH-PRESSURE TUBING

CROSS REFERENCE TO RELATED APPLICATIONS

This application claims benefit of U.S. Provisional Application No. 60/719,070, filed Sep. 21, 2005, the content of which is incorporated herein by reference.

TECHNICAL FIELD

The invention generally relates to tubing used in analytical instruments and other systems, and methods for making such tubing.

BACKGROUND INFORMATION

Various instruments utilize conduits for transportation of process fluids and sample compounds and/or for separation of sample compounds. For example, chemical-analysis instruments that utilize liquid chromatography (LC), capillary electrophoresis (CE) or capillary electro-chromatography (CEC) perform separation of sample compounds as the sample passes through a column. Such instruments include conduits or have connections to conduits that transport a variety of materials, such as solvents and sample compounds.

In addition to tubing, including separation column(s), liquid-chromatography instruments typically include reservoirs, pumps, filters, check valves, sample-injection valves, and sample compound detectors. Typically, solvents are stored in reservoirs, and delivered as required via reciprocating-cylinder based pumps. Sample materials are often injected via syringe-type pumps.

In some cases, separation columns include one or more electrodes to permit application of a voltage to a sample-containing fluid passing through and/or exiting from the conduit. CEC, for example, utilizes an electro-osmotic flow (EOF) to propel a mobile phase through a chromatographic column. In contrast, liquid chromatography, such as high-performance liquid chromatography (HPLC), relies on pressure to propel a fluid through a column.

Suitable analytical-instrument tubing withstands pressures encountering during fabrication and use, is reliable through repeated use, and has physical and chemical compatibility with process and sample compounds. Generally, a tube material should not corrode or leach, and sample compounds should not adhere to the tube (unless required for a separation process.)

For HPLC and higher-pressure applications, tubing is typically made from stainless steel or fused silica to provide suitable strength and cleanliness. Such tubing is typically joined to other components via stainless steel connectors.

Stainless steel, however, has disadvantages in some applications due to its biocompatibility limits in comparison to some other materials; some organic molecules tend to adhere to the inner walls of steel tubing, and components of a steel alloy at times leach into fluid passing through the tubing. Because organic molecules generally are less likely to stick to glass than to steel, steel tubing can be lined with glass to improve biocompatibility, but such tubing is vulnerable to breakage.

For good biocompatibility, tubing can be fabricated from suitable polymeric materials. To compensate for relatively poor strength, some polymer tubes have relatively thick walls with a fluid lumen produced by machining and polishing. Such columns are typically costly to manufacture. Moreover, the lumen surface is unsuitable for some applications.

Typically, tubing must also be compatible with connectors that provide fluidic connections to other components of an instrument. Problems associated with the design and use of connector fittings are particularly difficult for high-pressure fabrication and operation. For example, pressures in the range of 1,000-5,000 pounds per square inch (psi) or higher are often utilized in liquid chromatography.

SUMMARY OF THE INVENTION

One exemplary embodiment of the invention arises from the realization that tubing suitable for operation at pressures up to about 10,000 psi to 15,000 psi or greater and providing relatively good biocompatibility can be fabricated by inserting a polymeric tube in a high-strength outer tube, and melt bonding the polymeric tube to the outer tube. In one alternative, a portion of a polymeric inner tube is melted to form a bond between the inner tube and an outer metallic tube. In some embodiments, the bond prevents sliding movement of an inner tube relative to an outer tube and/or provides a leakage barrier for the interface between the inner and outer tubes.

Some embodiments of such tubing have a variety of advantages over some conventional tubing. For example, some embodiments are relatively easy and inexpensive to manufacture. Some of theses embodiments do not require injection molding to dispose a polymeric inner tube inside a high-strength outer tube. Some embodiments are compatible with commonly available metallic-based high-pressure connectors. Some of these embodiments are fabricated from standard stainless steel or titanium tubing that is suitable for operation at relatively high pressures.

Thus, as one example, a relatively high-pressure compatible and relatively biocompatible conduit is constructed at a relatively low cost from readily available components and integrated with other components of an analytical instrument by utilizing standard analytical-instrument connectors.

Accordingly, one embodiment of the invention features a method for making analytical-instrument tubing. At least one inner tube and at least one outer tube are provided for making the analytical-instrument tubing. The inner tube includes a polymeric material and the outer tube includes a material having a greater yield strength than the polymeric material. The inner tube is inserted into the outer tube and bonded to the outer tube. Bonding is accomplished by, in part, melting a portion of the polymeric material of the inner tube.

A second embodiment of the invention features an analytical-instrument tube. The tube includes inner and outer tubes. The inner tube is formed from a polymeric material, and the outer tube is formed from a material, such as a metallic material, that has greater yield strength than the polymeric material. A portion of the inner tube has a melt-bonded fixed contact to a portion of the interior surface of the outer tube. The fixed contact optionally provides a fluid-tight seal to impede fluid from leaking along the interface between the inner and outer tubes.

Another embodiment of the invention features an analytical instrument. The instrument includes a separation column, a transport tube, a solvent reservoir and pump, a sample injector, a detector to observe an eluent of the separation column, and a control unit that supports operation and data analysis.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DESCRIPTION

The phrases "chromatographic system," "chromatographic module," "chromatographic instrument," and the like herein refer to equipment used to perform chemical separations. Such equipment is a portion of an instrument that includes other components or is a standalone unit. Chromatographic equipment typically moves fluids under pressure and/or electrical forces.

Depending on context, the description provided herein of some illustrative embodiments of the invention interchangeably uses the words "tube," "conduit," "capillary," and/or "pipe." Depending on context, the word "capillary" refers to fused-silica tubes and/or refers to relatively narrow tubes. Tubes define an interior passageway, herein also referred to interchangeably as a lumen, bore, or channel. The word "column" herein refers to a tube that is used for separation of compounds in a sample, or is used to propel fluids in an electrokinetic pump.

The word "biocompatiblity" herein relates to the tendency of some organic materials to adhere to a particular tube material, as would be understood by one of ordinary skill. For example, fused silica is generally considered to be more biocompatible than is steel because organic molecules are typically less likely to adhere to fused silica than to a steel alloy.

Some embodiments of the invention involve instruments that include both chromatographic and mass-spectrometric components. In some of these embodiments, a chromatographic component is placed in fluid communication with a mass-spectrometric component through use of an appropriate interface, such as an electrospray-ionization interface. Some appropriate interfaces at times create or maintain separated materials in an ionic form and typically place a stream of fluid containing the ions into an atmosphere where the stream is vaporized and the ions are received in an orifice for mass-spectrometric analyses.

Figure 1:
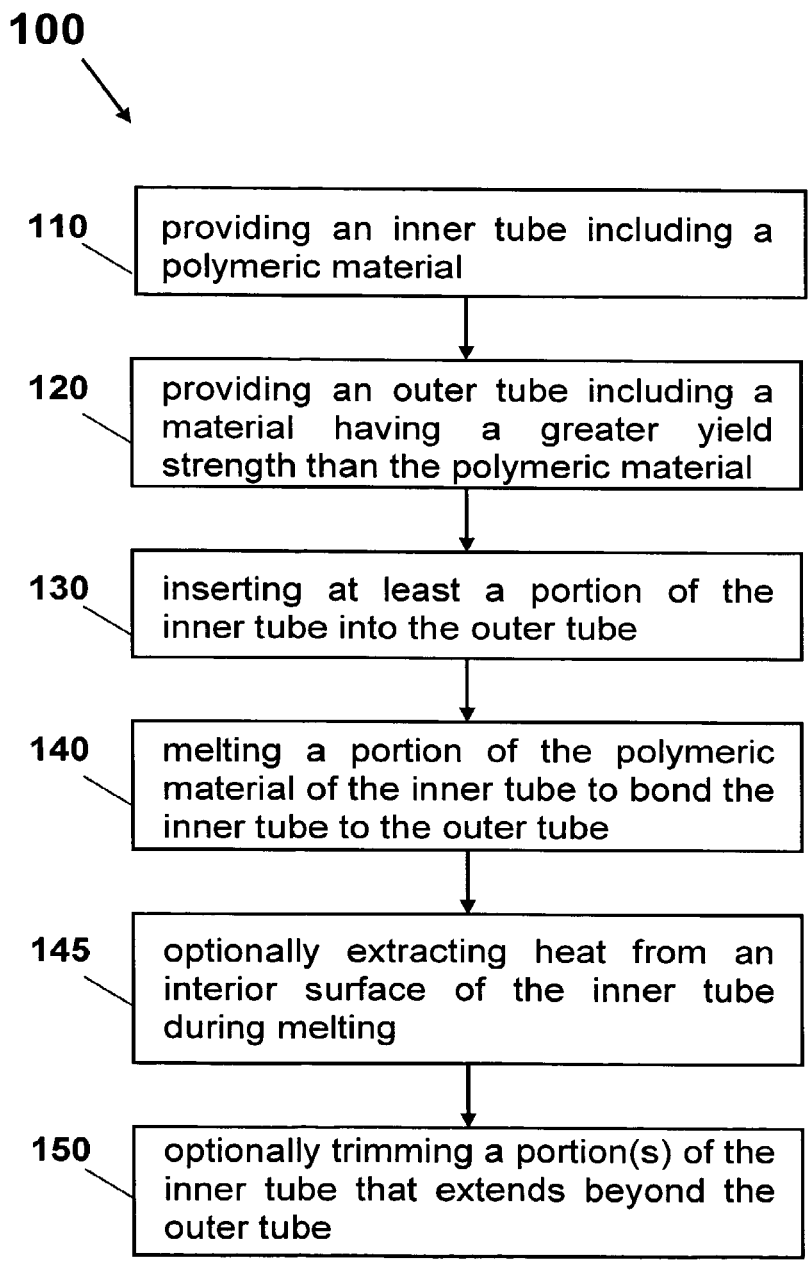
FIG. 1 is a flow diagram of a method for fabricating analytical-instrument tubing, in accordance with one embodiment of the invention.

FIG. 1 is a flow diagram that illustrates a method 100 for fabricating tubing for use in an analytical instrument, in accordance with one embodiment of the invention. The method 100 includes providing (Step 110) an inner tube that is formed at least in part from a polymeric material, providing (Step 120) an outer tube that is formed at least in part from a material having a greater yield strength than the polymeric material, inserting (Step 130) the inner tube into the outer tube, and bonding (Step 140) the inner tube to the outer tube by melting at least a portion of the polymeric material. Upon solidification of the melted portion, a fixed contact is formed between the inner and outer tubes.

Figure 2A:
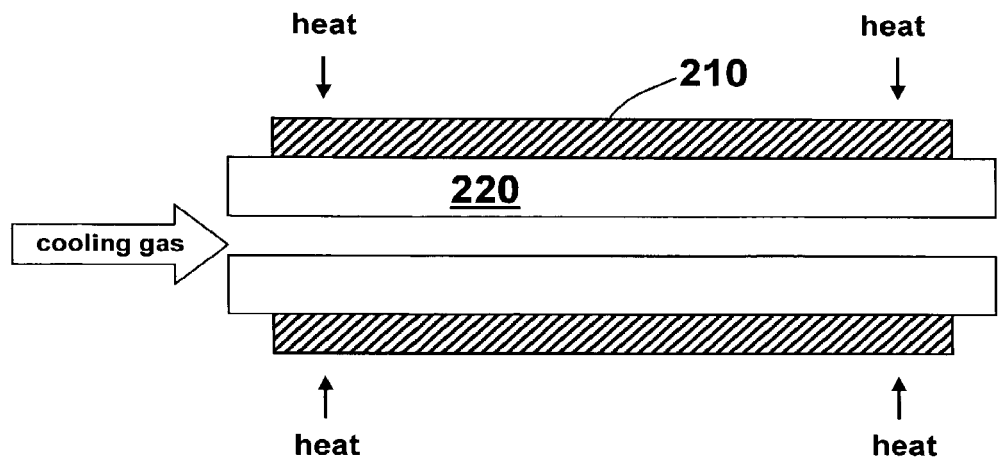
FIG. 2a is a cross-sectional diagram of tubing at an intermediate stage of fabrication, in accordance with one embodiment of the invention.
Figure 2B:
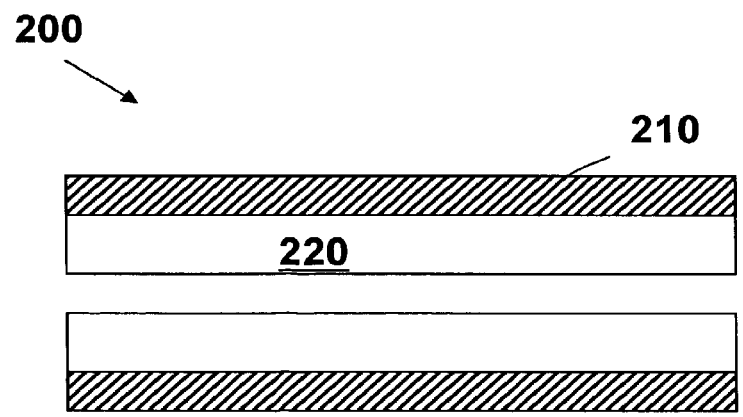
FIG. 2b is a cross-sectional diagram of the tubing of FIG. 2a at a later stage of fabrication.

Now also referring to FIG. 2a and FIG. 2b, the method 100 optionally includes extracting (Step 145) heat from an interior surface of the inner tube during melting, and/or includes trimming (Step 150) one or more portions of the inner tube after bonding the inner tube to the outer tube. FIG. 2a and FIG. 2b illustrate cross-sectional views of a tube 200 as it appears during heat extraction (Step 145) and after being trimmed (Step 150), in accordance with one alternative implementation of the method 100.

The tube 200 includes an outer tube 210 and an inner tube 220. As described in more detail below, the outer tube 210 is formed of a material that provides suitable strength and reliability while the inner tube 220 is formed of a material that provides melt-bonding capability and/or suitable biocompatibility. Upon completion of fabrication, the tube 200 is suitable for use as, for example, a transport conduit or column in a chromatographic system.

As illustrated in FIG. 2a, optionally, the inner tube 220 is initially selected to have a greater length than the length of the outer tube 210. In some embodiments of the method 100, the inner tube shrinks in length during bonding. Hence, selection of an inner tube 220 having a greater length in some cases avoids shrinkage of the inner tube 220 to a length less than that of the outer tube 220.

Subsequent to bonding of the inner tube 220 to the outer tube 220, if desired, the inner tube is trimmed (Step 150). In the illustrated example, the inner tube 220 is trimmed flush with the outer tube 210. In alternative embodiments of the invention, inner and/or outer tubes are trimmed and/or otherwise shaped as desired for compatibility with other components of an analytical system. Trimming (Step 150) in support of compatibility with conduit connectors is described below, in part with reference to FIG. 4.

The inner tube 220 defines a lumen through which material—such as solvent and/or sample material—flows. As described in more detail below, the outer tube 210 provides, in part, mechanical support while the inner tube 220 provides, in part, compatibility with a material flowing through the tube.

In various embodiments, the polymeric material is selected for its ability to form a melt bond to the outer tube and/or for its biocompatibility. For example, biocompatibility with proteins and peptides is important in some applications. In some embodiments, the inner tube is at least partially formed of any suitable meltable polymer, including known thermoplastic polymers.

The polyaryl-ether-ketones, for example, provide one class of thermoplastic polymers that also has good biocompatibility. One of the suitable polymeric materials of this class is polyether-ether-ketone, such as PEEK polymer (available from Victrex PLC, Lancashire, United Kingdom.)

Some embodiments utilize other polymers, for example, fluoropolymers such as polytetrafluorothylene (available as TEFLON polymer from Dupont Engineering Polymers, Newark, Delware), chlorotetrafluoroethylene, polychlorotrifluoroethylene (available as NEOFLON PCTFE fluoropolymer from Fluorotherm Polymers, Inc., Fairfield, N.J.), and modified copolymer fluoropolymers (for example, a modified copolymer of tetrafluoroethylene and ethylene available as DUPONT TEFZEL fluoropolymer, which is resistant to concentrated nitric acid or sulfuric acid), and other polymers, such as polyimide (available as DUPONT VESPEL polyimide.)

In some embodiments, the inner tube is formed of a composite material. For example, in some of these embodiments, the inner tub is formed of a mixture of a polymer, such as polyether-ether-ketone, and about 5% by weight of glass, fiberglass, carbon, and/or or other particles and/or fibers.

The material of the outer tube is selected from any suitable materials, including known materials, to provide, for example, a sufficient level of mechanical strength to support fabrication and/or operating conditions. In one embodiment, a desired level of mechanical strength is obtained by the combination of an outer tube(s) and an inner tube(s). For example, the materials and wall thicknesses of the inner and outer tubes are selected to perform HPLC (at, for example, about 2 kpsi to about 5 kpsi,) or to operate at higher pressures up to about 10 kpsi to 15 kpsi or higher.

Steel and titanium, for example, have relatively high yield strength, and are thus suitable for high-pressure operation of a transport tubing, column tubing, etc. For outer tubing, some embodiments utilize standard tubing known to those having ordinary skill in the high-pressure chromatographic arts. One suitable standard tubing is 1/16 inch outer diameter (OD) 316 alloy stainless steel tubing. The inner diameter (ID) of the steel tubing is selected as desired from, for example, standard available IDs. Standard IDs are available as small as about 4 mil (about 100 μm.)

In some embodiments, an OD of an inner tube is selected to provide a slidable fit within the selected outer tubing. An ID of an inner tube is selected as desired. For example, an ID can be selected to be as small as about 2 mil (about 50 μm) or less.

After inserting (Step 130) the inner tube, bonding is initiated by heating (Step 140) sufficiently to melt at least a portion of the inner tube adjacent to the inner surface of the outer tube. Upon cooling, the melted portion solidifies and forms a fixed contact between the inner and outer tubes.

The inner tube is heated in any suitable manner. In one embodiment, the inner tube is heated indirectly by heating an adjacent portion of the outer tube. For example, the inner tube is heated by heating the outer tube sufficiently to raise the temperature of portions of the inner tube to at least a melting point temperature.

For example, in some embodiments, the entire outer tube is heated, uniformly or non-uniformly. In other embodiments, heat is directed only to one or more portions of the outer tube. As illustrated in FIG. 2a, in one embodiment, heat is directed to end portions of the outer tube 210. In one alternative of this embodiment, two bonded regions are formed to restrict movement of the inner tube 220 within the outer tube 210 and to restrict leakage of fluid past the bonded regions into the non-bonded interfacial space between the inner and out tubes 210, 220.

Heat is directed at the outer tube in any suitable manner, including known heating methods. For example, the inner and outer tubes, or portions of the tubes, are placed in one or more ovens or in cavities of heatable blocks of aluminum or steel. Such blocks are heated by, for example, resistive heaters or a heated platten. Other options for heating, such as induction heating, are available and any suitable method may be used. Various embodiments utilize any method of heat transfer that provides the desired bonding temperature and environment.

The portion of the inner tube that is melted (Step 140) has its temperature profile controlled as desired. For example, the temperature is raised gradually to a desired temperature over a period of seconds or minutes or hours. Alternatively, the portion of the inner tube is melted nearly instantaneously. In some embodiments, a suitable temperature profile that supports a good bond is empirically or theoretically determined.

In some embodiments, heating over a period of several minutes is helpful to obtain a good bond. It is desirable in some cases to controllably heat and melt the portion of the inner tube to obtain repeatable results and to avoid incorporation of bubbles or voids within a bonded region.

In some embodiments, it is undesirable to overheat the polymeric material of the inner tube when thermal breakdown or decomposition is possible. One embodiment utilizes a non-oxidizing atmosphere during heating.

After heating, the inner and outer tubes are either passively or actively cooled to ambient temperature. Cooling is accelerated by, for example, any suitable method that maintains the chemical and structural integrity of the bond and components.

Some alternative implementations of extracting (Step 145) heat during melting (Step 140) are now described. To extract heat, a fluid, such as a gas or liquid, is directed through a lumen defined by the innermost tube. In some embodiments, the fluid is a substantially inert gas, such as nitrogen or argon.

The fluid is used, for example, to ensure that melting remains localized and does not extend to the inner surface of the polymeric-material tube. The fluid is thus used, in some cases, to maintain a passageway through the inner tube during melting (Step 140).

In one embodiment, the flow of a gas through the tube is controlled by monitoring the pressure drop of the gas across the tube (i.e., the difference in pressure between an inlet end and an outlet end of the tube.) Desirable pressure drops are, for example, in a range of about 10 psi to about 100 psi. An increase in the selected pressure drop is often desirable for greater lengths of tubing and/or for smaller diameters of a passageway.

A suitable pressure drop is determined, for example, empirically. For particular selected materials and tube dimensions, a suitable pressure is determined at which the passageway through the tube remains open during bonding.

In one embodiment, gas is directed into the tube at one end of the tube while a portion of the tube adjacent to the opposite end of the tube is heated to form a bond adjacent to that end. Gas is then directed into the bonded end of the tube, and the now opposite end is heated to form a bond adjacent to that end. In this manner, a passageway is maintained through a lumen having an ID of as small as about 50 μm or less.

The remaining description, below, is directed primarily to some embodiments that utilize a steel outer tube and a polyether-ether-ketone inner tube. One having ordinary skill will understand, however, that principles of the invention are applicable to a broader range of materials and processing conditions.

Melting (Step 140), in one illustrative case, is obtained by heating portions of the inner tube to a temperature somewhat above the melting point temperature. In one embodiment, for example, the polyether-ether-ketone portion is heated to a temperature of between about 385° C. to about 405° C. The polymer is heated at the desired temperature for a period of time of about 1 to about 3 minutes, although the invention is not limited to such. It is often desirable to heat neighboring portions of the inner and outer tubes to a similar or same temperature during melting (Step 140) to obtain a good bond between the inner and outer tubes.

In one illustrative embodiment, an analytical-instrument tube includes an inner tube and an outer tube of the following dimensions and composition. The outer tube is formed of drawn 316 stainless steel and the inner tube is formed of extruded polyether-ether-ketone. The inner tube has an inner diameter (ID) of 2 mil (50 μm) or 2.5 mil (60 μm). The outer tube has an outer diameter of 1/16 inch, and has an ID selected to be compatible with the OD of the inner tube. The word "compatible" is herein used to mean that the inner tube can be inserted into the outer tube. Preferably, during insertion, the inner tube is not damaged and there is some contact around the circumference of the inner tube, i.e., there is a minimal gap between the inner and outer tubes. One having ordinary skill will understand this example is merely illustrative and non-limiting.

Optionally, more than one inner tube and/or more than one outer tube are utilized to fabricate tubing. For example, some embodiments entail fabrication of a conduit including two or more outer tubes disposed in a row (along the conduit) and/or disposed within one another. For example, in one embodiment, multiple inner tubes are inserted serially, one after another, into an outer tube. In another embodiment, multiple inner tubes are disposed side-by-side, so that the inner tubes provide multiple passageways through the completed tubing. Portions of one or more of the inserted inner tubes are then melted to bond the tubes to each other and/or to the outer tube or tubes.

In another embodiment, inner tubes are inserted within one another. In still another embodiment, outer tubes are inserted within one another. Thus, some embodiments include more than two concentrically disposed tubes. One such embodiment is described in more detail with reference to FIG. 3.

Figure 3:
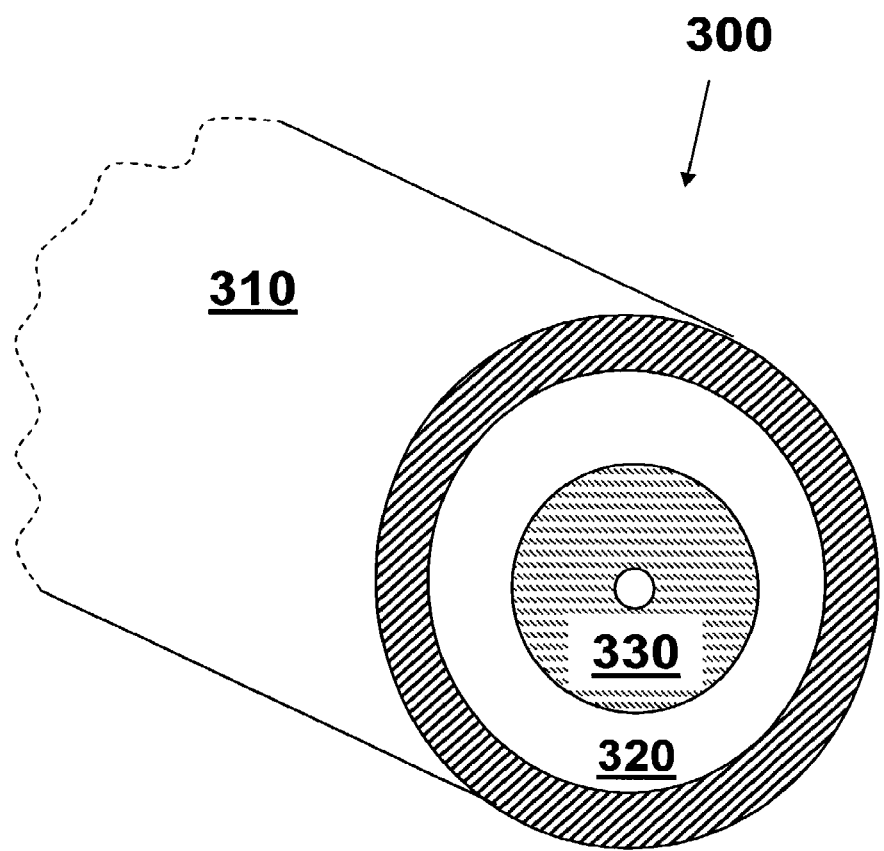
FIG. 3 is an angled end view of a tube, in accordance with one embodiment of the invention.

FIG. 3 illustrates a three-dimensional angled end view of a tube 300, in accordance with another illustrative embodiment of the invention. The tube 300 includes an outer tube 310, an inner tube 320 and a second inner tube 330 (herein also referred to as a liner tube.)

The outer, inner, and liner tubes 310, 320 330 are each fabricated in any desired dimensions in any suitable manner from any suitable materials, including known fabrication methods and materials. For example, the outer tube 310 and the inner tube 320 optionally have some or all of the compositional and dimensional features, respectively, of the inner tube 210 and the outer tube 210 described above.

The liner tube 330 optionally is a fused-silica capillary. The inner tube 320 optionally is melted bonded to the outer tube 310 and/or the liner tube 330. Thus, as one example, the tube 300 has a steel outer tube 310, a thermoplastic-polymer inner tube 320 and a fused-silica liner tube 330. The example tube 300 provides the high-pressure reliability and durability of steel tubing in conjunction with the biocompatible properties of a fused-silica capillary for contact with fluids passing through the tube 300.

In view of the description provided herein of illustrative embodiments fabricated from two or more inner and outer tubes, numerous alternative configurations will be apparent to one having ordinary skill in the chemical separation arts. For example, some embodiments include two or more concentric outer tubes and/or two or more concentric inner tubes. Inner and outer concentric tubes are alternated, in some embodiments, such that, for example, an inner tube is disposed between two outer tubes and/or an outer tube is disposed between two inner tubes.

Returning to FIG. 1, the method 100 is useful for fabricating tubing of a great variety of lengths. For example, tubing having a length of about 1 inch or less up or a length of up to 6 feet or greater is amenable to relatively easy fabrication via the method 100. Although not required, standard lengths of commercially available tubing are amenable for use with the method 100. A specific desired final length is obtained in some embodiments by cutting outer and/or inner tubes prior to inserting (Step 130) or by cutting the tubing after inserting (Step 130).

The method 100 is used to fabricate both straight and curved tubing, or other desired configurations. For example, in one embodiment a length of metallic tubing is bent at one or more sections to provide a desired configuration for use in a particular analytical instrument. An inner tube is inserted (Step 130) before or after bending of the outer tube. Alternatively, an outer tube is manufactured with a non-straight configuration so that bending is not required.

Tubes according to many embodiments of the invention are well suited for use with tubing connectors, such as standard connectors known to those having ordinary skill in the separation arts. It should also be understood that the above-described and below-described and illustrated configurations are not intended to limit application of the invention to any particular type of connector presently available or envisioned or yet to be developed. Moreover, end portions of tubes, according to some embodiments of the invention, are configured to mate with desired types of connectors. For example, in some embodiments, an inner or outer surface of an end portion of the tube is threaded to mate with a threaded connector.

Merely as one illustrative example, convenient use of a tube with a standard connector is described with reference to FIG. 4.

Figure 4:
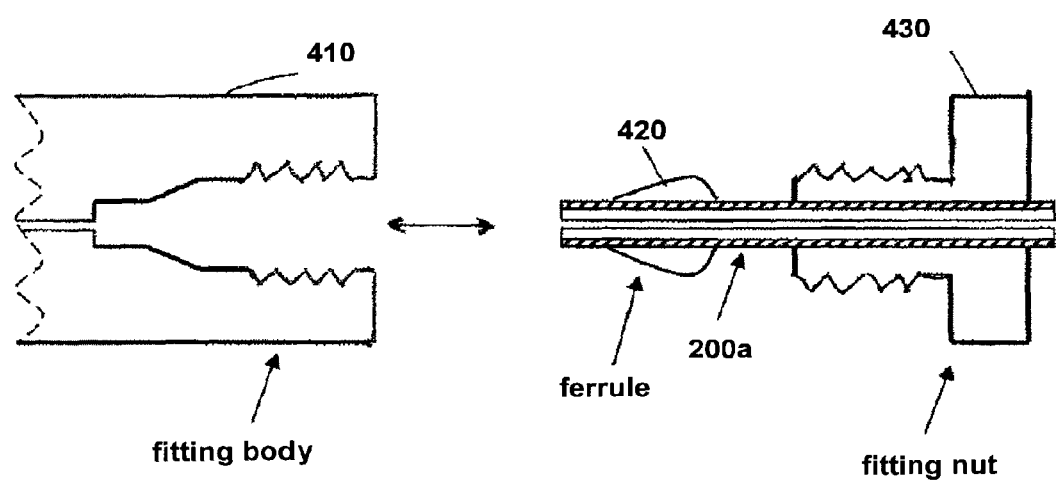
FIG. 4 is a cross-sectional diagram of a portion of a connector and a tube, in accordance with one embodiment of the invention.

FIG. 4 illustrates a cross section of a tube-and-connector assembly, in accordance with one embodiment of the invention. The assembly includes a tube 200a and conventional connector components that include a fitting body 410, a ferrule 420, and a fitting nut 430. The tube 200a is, for example, fabricated according to the method 100 and/or is similar in construction to the tubes 200, 300 described above. A threaded portion of the fitting nut 430 mates with a threaded portion of the fitting body 410. The fitting nut 430, when tightened into the fitting body 410, compresses the ferrule 420 against the tube 200a to provide a seal against leaks.

Only the proximal end of the fitting body 410 is shown in FIG. 4. The distal end of the fitting body 410 has any desired configuration, including standard configurations. For example, the distal end may be configured as is the proximal end, i.e., to connect to a second tube. Thus, the connector is used, for example, to connect the tube 200a to another tube of similar or different OD, to a separation column, or to another component of an analytical instrument.

In view of the above description, one having ordinary skill in the separation arts will understand that the tubes 200a, 200, 300 may be used in conjunction with any suitable connectors, including known connectors.

In view of the description contained herein, it will be apparent to one of ordinary skill that many other connectors are usable with various tubing embodiments of the invention. For example, some suitable connectors utilize a two-ferrule system. Such connectors have applications, for example, in high-pressure environments, for example, at pressures up to about 15,000 psi and greater.

One example of a connector that is suitable for use at very high pressure is the Swagelok gaugeable SAF 2507 super duplex tube fitting (available from the Swagelok Company, Solon, Ohio.) This connector includes front and back ferrules formed from different steel alloys. The back ferrule drives the front ferrule into a fitting body and onto the surface of a tube to create a seal.

Figure 5:
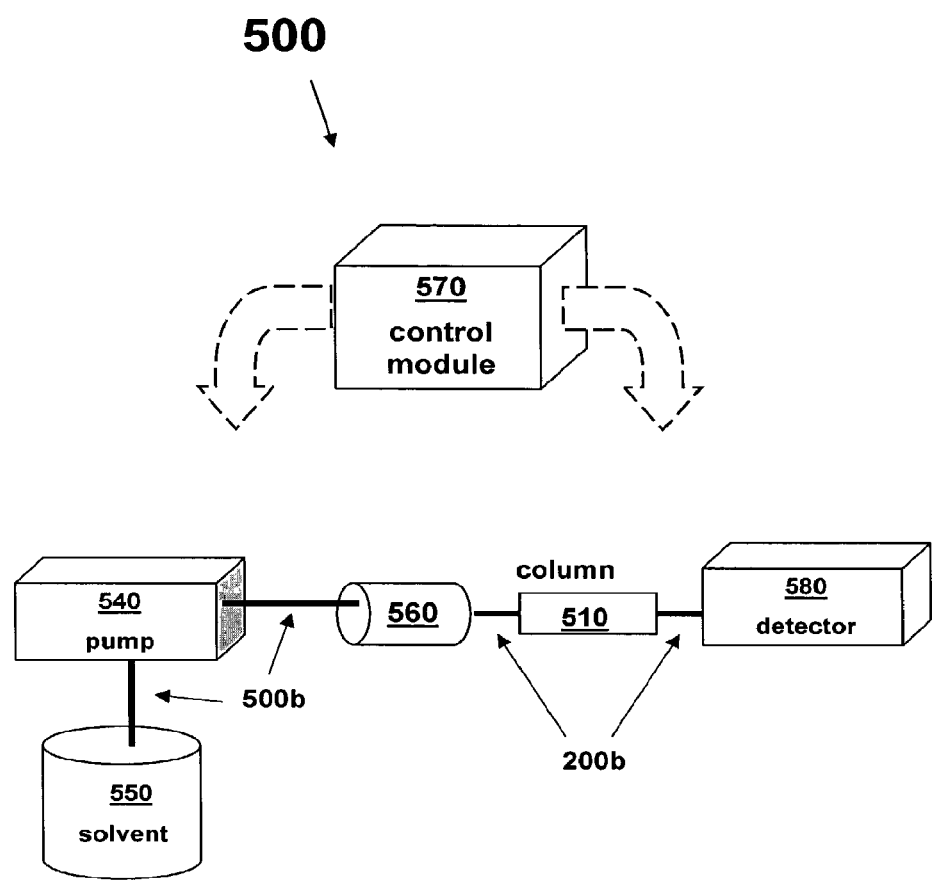
FIG. 5 is a block diagram of an analytical instrument, in accordance with one embodiment of the invention.

FIG. 5 is a block diagram of an analytical instrument 500, in accordance with one embodiment of the invention. The instrument 500 includes a separation column 510, a solvent reservoir 550, a solvent pump 540, a sample injector 560, a detector 580, tubing 500b connecting the pump 540 to the reservoir 550 and the injector 560, tubing 200b connecting the column 510 to the injector 560 and the detector 580, and a control module 570. Some or all of the tubing 200b has features similar to those described above with reference to FIG. 1, FIG. 2a, FIG. 2b and/or FIG. 3.

In some implementations, the instrument 500 is a known high-pressure chromatographic instrument, though modified to include tubing 200b in accordance with the above described features.

The control module 570—including, for example, a personal computer or workstation—receives data and/or provides control signals via wired and/or wireless communications to, for example, the pump 540, the injector 560, and/or the detector 580. The control module 570 supports, for example, automation of sample analyses. The control module 570, in various alternative embodiments, includes software, firmware, and/or hardware (e.g., such as an application-specific integrated circuit), and includes, if desired, a user interface.

Variations, modifications, and other implementations of what is described herein will occur to those of ordinary skill in the art without departing from the spirit and the scope of the invention as claimed. For example, though the embodiments of tubes illustrated herein have circular cross sections, the invention encompasses tubes that have non-circular cross sections. Accordingly, the invention is to be defined not by the preceding illustrative description but instead by the spirit and scope of the following claims.

What is claimed is:

1. A method for making tubing, comprising:
providing an inner tube comprising a polymeric material;
providing an outer tube comprising a material having a greater yield strength than the polymeric material;
inserting at least a portion of the inner tube into the outer tube; and
bonding the inner tube to the outer tube, wherein bonding comprises melting at least a first portion of the polymeric material of the inner tube after inserting, wherein the melted first portion of the polymeric material of the inner tube is adjacent to an end of the outer tube and wherein extracting heat comprises extracting sufficient heat to maintain a passageway through a lumen defined by the interior surface of the inner tube, wherein extracting heat comprises extracting sufficient heat to maintain a passageway through a lumen defined by the interior surface of the inner tube, and wherein extracting heat further comprises maintaining a substantially solid inner surface of the inner tube, and wherein extracting heat comprises flowing a fluid comprising a substantially inert gas through the lumen of the inner tube.

2. The method of claim 1, wherein the melted first portion of the polymeric material forms a bond that substantially prevents fluid leakage along an interface between the outer and inner tubes.

3. The method of claim 1, wherein the melted first portion of the polymeric material substantially surrounds the inner tube.

4. The method of claim 1, wherein bonding comprises melting the first portion and a second portion of the polymeric material, wherein the first and second portions are adjacent to opposite ends of the outer tube and bound an unmelted portion of the inner tube.

5. The method of claim 1, wherein melting comprises heating portions of the outer tube adjacent to opposite ends of the outer tube without substantially heating an intermediate portion of the outer tube.

6. The method of claim 1, wherein providing the inner tube comprises selecting a length of the inner tube to be greater than a length of the outer tube.

7. The method of claim 6, wherein the length of the inner tube is selected to accommodate shrink-back of the inner tube during bonding.

8. The method of claim 6, wherein inserting comprises disposing the inner tube in the outer tube so that opposite end portions of the inner tube extend beyond associated ends of the outer tube.

9. The method of claim 8, further comprising trimming the end portions of the inner tube substantially flush with the ends of the outer tube after bonding.

10. The method of claim 1, wherein bonding comprises maintaining an unmelted portion of the polymeric material of the inner tube in a substantially solid state while melting the first portion of the polymeric material of the inner tube.

11. The method of claim 1, wherein a combined mechanical strength of the bonded outer and inner tubes is sufficient to perform liquid chromatography at a pressure of about 15 Kpsi or greater.

12. The method of claim 1, wherein providing the inner tube comprises providing a plurality of inner tubes, and inserting comprises inserting the plurality of inner tubes in a serial or a parallel arrangement.

13. The method of claim 1, wherein the material of the outer tube comprises a material selected from the group of materials consisting of steel, titanium, and silica.

* * * * *